United States Patent [19]

Geria

[11] Patent Number: 4,990,136
[45] Date of Patent: Feb. 5, 1991

[54] SUPPOSITORY APPLICATOR

[75] Inventor: Navin M. Geria, Warren, N.J.

[73] Assignee: Warner-Lambert Company, Morris Plains, N.J.

[21] Appl. No.: 420,797

[22] Filed: Oct. 12, 1989

[51] Int. Cl.⁵ .......................................... A61M 31/00
[52] U.S. Cl. ......................................... 604/63; 604/59
[58] Field of Search ............................. 604/11, 14–18,
604/54–61, 63, 117, 134, 135, 285, 288;
222/518, 336, 339; 221/271, 276; 124/16

[56] References Cited

U.S. PATENT DOCUMENTS

| 17,000 | 4/1957 | Somernille | 604/59 |
| 1,868,308 | 7/1932 | Brumfield | 604/59 |
| 2,007,626 | 7/1935 | Waring | 604/59 |

FOREIGN PATENT DOCUMENTS

| 2122091 | 11/1972 | Fed. Rep. of Germany | 604/15 |
| 573719 | 3/1958 | Italy | 604/59 |
| 0001190 | of 1895 | United Kingdom | 604/59 |
| 0006047 | of 1895 | United Kingdom | 604/59 |
| 0956679 | 4/1964 | United Kingdom | 604/15 |

Primary Examiner—John D. Yasko
Assistant Examiner—A. Gutowski
Attorney, Agent, or Firm—Charles A. Gaglia, Jr.

[57] ABSTRACT

A suppository applicator for inserting suppositories into body cavities comprises a tubular body having an open end and a closed end. A plunger is slidably disposed in the tubular body for reciprocal movement between a withdrawn position and an extended position and a combined spring is situated between the plunger and the closed end of the applicator to urge the plunger toward its extended position. The tubular body is formed with a longitudinal slot along its side which has a notch that extends from the slot to engage a latch on the plunger and hold the plunger in its withdrawn position. The open end of the tubular body is shaped to stationarily hold a suppository against the withdrawn plunger until the suppository is to be inserted into the body cavity. When the latch is released, the spring pushes the plunger against the suppository to insert the suppository into its desired placement in the body cavity.

8 Claims, 2 Drawing Sheets

SUPPOSITORY APPLICATOR

FIELD OF THE INVENTION

The present invention pertains to applicators for inserting suppositories into a body cavity. More specifically, the present invention pertains to devices which insert suppositories into a body cavity using a spring driven plunger. This invention is particularly, but not exclusively, useful for inserting anal suppositories.

BACKGROUND OF THE INVENTION

In the health care industry, it is well known that there are many ways by which medication can be administered to a patient. For example, medicine can be either swallowed, inhaled, injected or inserted into a body cavity. When it is necessary for the medicine to be gradually absorbed into the body, suppositories which can be inserted into an appropriate body cavity have been particularly effective.

When suppositories are used, physicians ofttimes use manual applicators to assist in inserting the suppository into the body cavity because they provide a safe, reliable and hygenic means for controlling the insertion of the suppository. Additionally, applicators can be used by the patient as a convenient aide for self-insertion when a physician is not needed. To accomplish their purpose, most applicators typically incorporate a tube which holds the suppository while a plunger is manually advanced through the tube to push the medicine into the cavity. Sometimes, however, manual force on the plunger is inadequate for the accomplishment of the task.

In veterinary medicine, manual pressure is often ineffective because of the uncooperative nature of the particular animal. For example, to prevent an animal from spitting out the medicine, veterinarians use spring loaded applicators to shoot the suppository past the soft-pallet in the animal's throat. The spring driven plunger supplies a quick, forceful thrust to the suppository which propels the medicine into the animal's esophagus before it can be disgorged by the animal. One such spring applicator is disclosed in U.S. Pat. No. 199,849 to Middleditch. This particular applicator comprises a tapered tube with a spring driven plunger positioned inside the tube. Once the plunger is retracted, a clip holds it in position until the suppository is ready to be released. The applicator is then placed in an animal's mouth and the plunger is released to propel the suppository down the animal's throat before it can be regurgitated.

As implied above, it is sometimes desirable to insert suppositories into the body cavity of a human being such as the rectum or the vagina. Although conventional spring applicators may work well for the injection of medicinal suppositories into the mouths of animals, due to the violent nature of the forces that are applied, use of these applicators can be painful or even dangerous when used for anal or vaginal insertion on humans. Consequently, manual applicators, as opposed to spring loaded applicators, have been more often used for inserting suppositories into humans. As an example, U.S. Pat. No. 1,538,678 to Blinn employs a tapered tube similar to Middleditch, except that the plunger is manually operated. Unfortunately, manual applicators are subject to the inexperience of the user. Consequently, the force applied on the plunger can be unpredictable and even ineffective. On the other hand, while the applicators that use a mechanical force are more reliable in providing a predictable result, they tend to propel the suppository with a sudden, peaking force which makes anal insertion uncomfortable and which runs the risk of traumatizing the anal canal.

The present invention recognizes the desirability of a suppository applicator which provides a constant, but gentle force on the plunger in order to minimize the danger of tearing or injuring the rectal wall. The present invention also recognizes that this can be accomplished by mechanical means once the bolus of medicine is placed at the cavity orifice.

In light of the above, the present invention provides a suppository applicator which can be repetitively operated to hygenically insert suppositories into body cavities with consistency. The present invention also provides a mechanical suppository applicator that has a prolonged useful life. Further, the present invention provides an applicator that inserts suppositories into a body cavity with ease under a substantially constant linear force. Additionally, the present invention provides a suppository applicator which is simple to sue, is easily manufactured and is comparatively costeffective.

SUMMARY OF THE INVENTION

The preferred embodiment of a suppository applicator according to the present invention includes a tubular body with a closed end, and an open end which is formed with an adaptor to hold the suppository. The tubular body is formed with a longitudinal slot along its side and has a notch which extends from the slot. A plunger is disposed in the tube and slides back and forth between an extended position and a withdrawn position. A latch is attached to the plunger and extends through the slot for reciprocal movement with the plunger. Further, the latch is engageable with the notch to hold the plunger in its withdrawn position. A spring mechanism is disposed between the plunger and the closed end of the tube and is biased to urge the plunger toward its extended position. For the present invention, the spring mechanism is a so-called combined spring that includes a first spring which is in a state of tension over a specified length and a second spring which is in a state of compression over the same length. The two springs are juxtaposed and connected to each other at their respective ends so, that in a state of equilibrium, the first spring is in a state of compression and the second spring is in a state of tension.

In its operation, the spring mechanism is compressed as the plunger is retracted into the tube to its withdrawn position. When the plunger is withdrawn, the latch is engageable with the notch to hold the plunger in its withdrawn position. A suppository is then placed in the adaptor at the open end of the applicator body in contact with the end of the plunger and positioned at the orifice of the body cavity. Upon release of the latch from the notch, the spring mechanism urges the plunger forward to gently insert the suppository into the body cavity as the spring force overcomes any reactive resistance from the structure or muscle response in the cavity.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
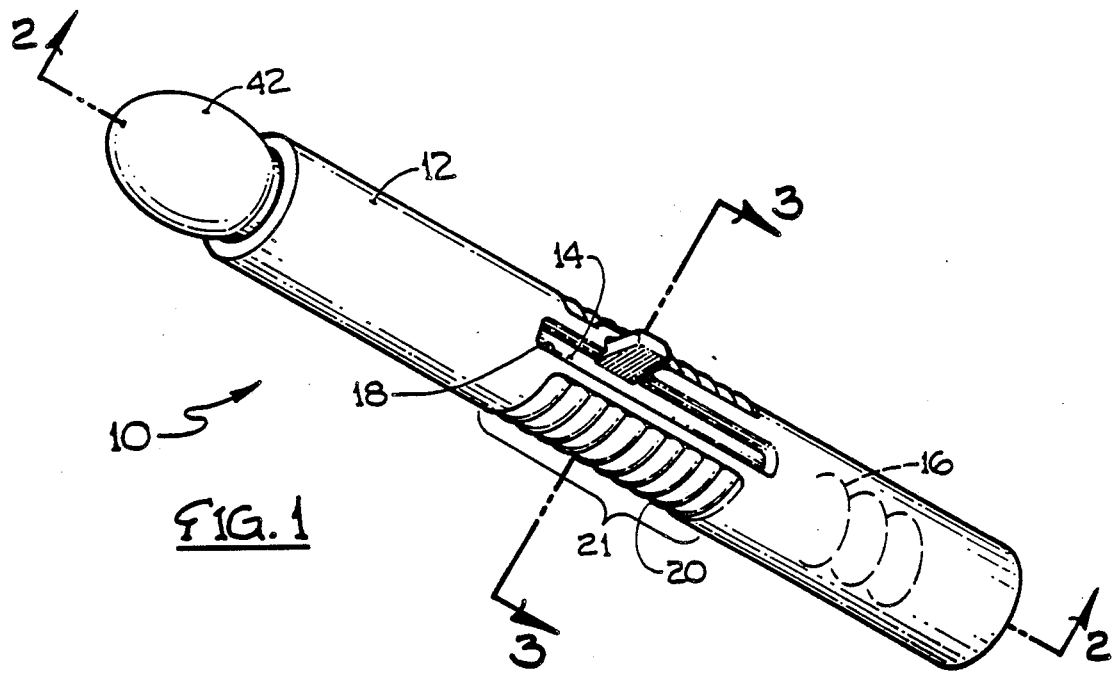
FIG. 1 is a perspective view of the applicator and a suppository positioned thereon.
Figure 4:
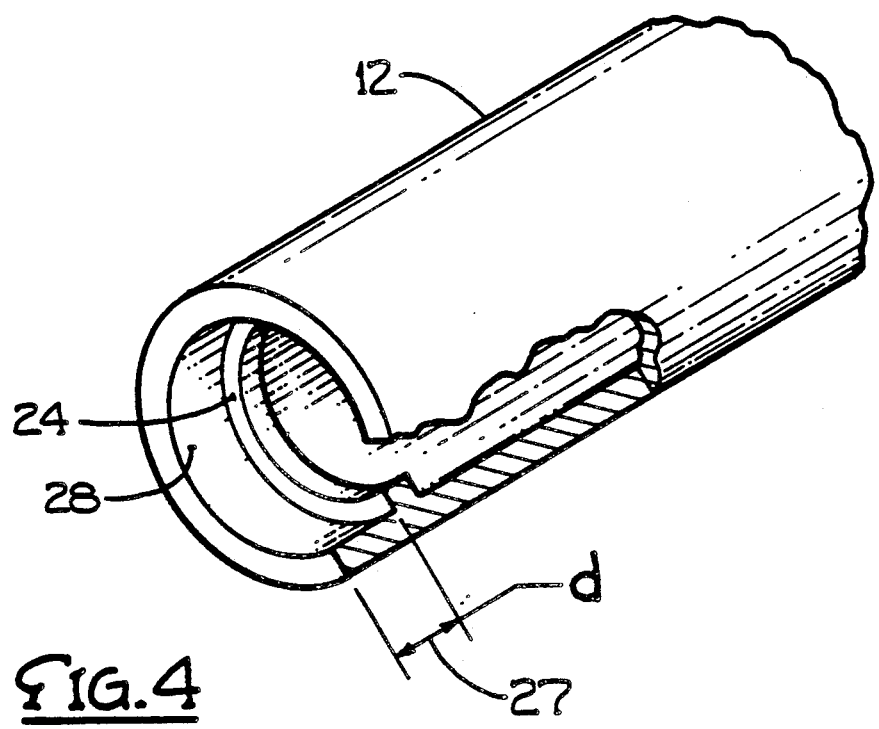
FIG. 4 is a perspective view of the adapter of the applicator, with portions of the applicator body broken away.

Referring initially to FIG. 1, a suppository applicator according to the present invention is shown and generally designated 10. As seen, applicator 10 comprises a hollow tubular body 12, cylindrical plunger 14 and spring mechanism 16. Tubular body 12 is an elongated barrel which is formed with a longitudinal slot 18 and is textured on its exterior surface 20 in the region 21 to facilitate holding applicator 10. As perhaps best seen in FIG. 2A, tubular body 12 is also formed with a notch 22 on the edge of slot 18. As shown in both FIGS. 2 and 4, tubular body 12 is further formed with an adaptor 24 at its open end 28. More specifically, adaptor 24 is formed as a recess 26 which extends a distance 27 from the open end 28 of tubular body 12. It is to be appreciated that the distance 27 can be varied according to the type of suppository 42 which applicator 10 is designed to accommodate. As will be appreciated by the ordinary consumer, suppositories vary in size and shape depending on their intended use (i.e. vaginal or anal) and the particular manufacturer. Preferably, tubular body 12 is made of a material such as a washable and durable hard plastic which is of sufficient strength to rigidly house the interactive components of applicator 10.

Figure 2A:
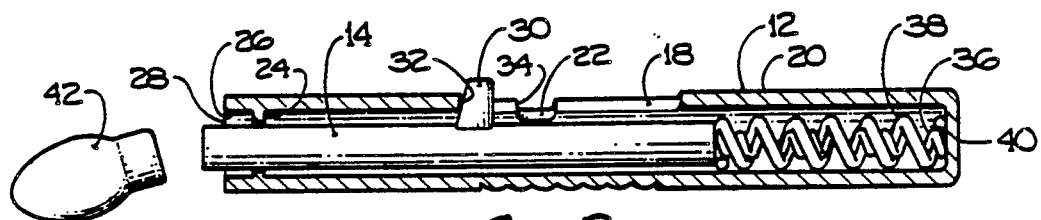
FIG. 2A is a cross-sectional view of the applicator as seen along the line 2—2 in FIG. 1 with the plunger in its extended position.
Figure 2B:
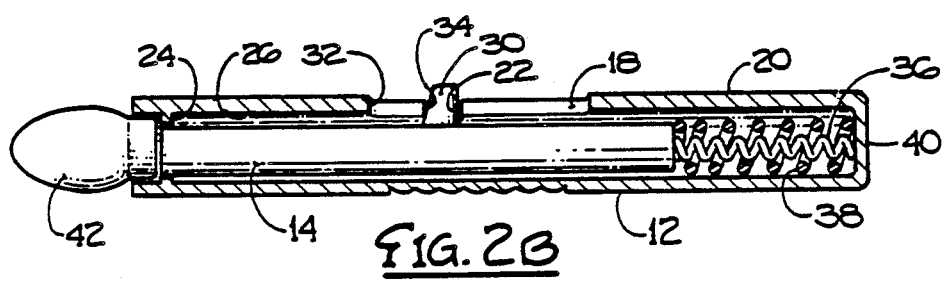
FIG. 2B is a cross-sectional view of the applicator as seen in FIG. 2A with the plunger in its withdrawn position and a suppository placed on the adaptor of the applicator.
Figure 3:
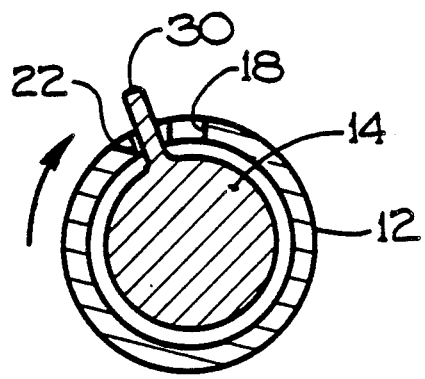
FIG. 3 is a cross-sectional view of the applicator as seen along the line 3—3 in FIG. 1.

Inside tubular body 12, a cylindrical plunger 14 is positioned to slide between an extended position (FIG. 2A) and a withdrawn position (FIG. 2B). As shown, plunger 14 is formed with a latch 30 which protrudes through the slot 18 and freely slides back and forth along slot 18 as plunger 14 moves back and forth in tubular body 12. At its extended position, plunger 14 is restrained from any further forward extending movement when the latch 30 contacts abutment 32 of tubular body 12 at the forward end of slot 18. When plunger 14 is retracted to its withdrawn position, latch 30 can be rotated into notch 22, and placed in contact with abutment 34 to restrain plunger 14 from sliding forward.

Still referring to FIGS. 2A and 2B, it is seen that spring mechanism 16 is preferably a combined spring which comprises a first spring 36 and a second spring 38 that are disposed together between plunger 14 and closed end 40 of tubular body 12. First spring 36 and second spring 38 are juxtaposed and connected to each other at their respective ends in a manner which places spring 36 in compression and spring 38 in tension when joined. When disposed in tubular body 12, spring mechanism 16 is biased to urge plunger 14 from its withdrawn position toward its extended position.

As seen in FIG. 2B, when plunger 14 is in its withdrawn position, first spring 36 is in tight compression while second spring 38 is slightly tensed. As the plunger 14 moves toward its extended position, however, second spring 38 is placed in a progressively higher state of tension. This dampens the expansive movement of first spring 36 and causes the combined spring 16 to provide a more controlled linear force on plunger 14.

OPERATION

In its operation, suppository applicator 10 is primarily intended to administer anal suppositories to a patient. As seen in FIG. 1, plunger 14 is retracted to its withdrawn position and restrained by latch 30 which is slipped into notch 22. At this point the extending action on plunger 14 by spring mechanism 16 is counteracted by the engagement of latch 30 with notch 22. A suppository 42 is then placed on adaptor 24 at the open end 28 of body 12. Upon release of latch 30, spring mechanism 16 urges plunger 14 to slide forward to its extended position to insert suppository 42 into the body cavity.

While the particular suppository applicator as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A suppository applicator which comprises:
    a cylinder formed with a longitudinal bore, having an open end and a closed end, said open end adapted for holding a suppository;
    a plunger disposed in said cylinder for movement between an extended position, and a withdrawn position; and
    a compound spring disposed between said plunger and said closed end of said cylinder to urge said plunger toward said extended position.

2. A suppository applicator as recited in claim 1 further comprising a means for holding said plunger in said withdrawn position.

3. A suppository applicator as recited in claim 1 wherein said holding means is a rotatable latch for releasably holding said plunger in said withdrawn position.

4. A suppository applicator comprising:
    a body having an open end and a closed end, said open end adapted for holding a suppository;
    a plunger disposed in said body for movement between an extended position and a withdrawn position, said plunger having a first end and a second end; and
    a compound spring disposed in said body between said second end of said plunger and said closed end of said body to urge said plunger toward said extended position under a substantially constant force to disengage said suppository from said applicator, said compound spring comprising a first spring and a second spring, said first spring in a state of tension at a specified length and said second spring in a state of compression over the same length.

5. A suppository applicator as recited in claim 4 further comprising a latch for holding said plunger in said withdrawn position.

6. A suppository applicator as recited in claim 5 wherein said latch is rotatable for releasing said plunger from said withdrawn position, allowing said plunger to move to said extended position to disengage said suppository from said applicator.

7. A suppository applicator comprising:
   a tubular body having an open end and a closed end, said open end formed with a recess for holding a suppository;
   a plunger disposed in said body for movement between an extended position and a withdrawn position, said plunger having a first end and a second end; and
   a compound spring comprising a first spring in a state of tension at a specified length and a second spring in a state of compression over the same length to urge said plunger toward said extended position under a substantially constant force to disengage said suppository from said holding means.

8. A suppository applicator as recited in claim 7 further comprising a means for releasably holding said plunger in said withdrawn position.

* * * * *